United States Patent [19]
Hutchings

[11] 4,136,123
[45] Jan. 23, 1979

[54] USE OF WATER SOLUBLE METALLO PHTHALOCYANINES AS OXIDATION CATALYSTS

[75] Inventor: David A. Hutchings, Stow, Ohio

[73] Assignee: The Goodyear Tire & Rubber Company, Akron, Ohio

[21] Appl. No.: 490,424

[22] Filed: Jul. 22, 1974

[51] Int. Cl.$^2$ .............................................. C07C 179/04
[52] U.S. Cl. ..................................... 568/565; 568/575
[58] Field of Search ........... 260/610 B, 593 A, 632 C, 260/610 A

[56] References Cited

U.S. PATENT DOCUMENTS

| | | | |
|---|---|---|---|
| 2,954,405 | 9/1960 | Hock et al. ...................... | 260/610 B |
| 3,634,328 | 1/1972 | Brownstein et al. ............ | 252/431 N |
| 3,883,243 | 4/1974 | Brownstein et al. ............. | 260/610 B |

*Primary Examiner*—James O. Thomas, Jr.
*Assistant Examiner*—Werren B. Lone
*Attorney, Agent, or Firm*—J. Y. Clowney

[57] ABSTRACT

Metallo phthalocyanines which have been rendered water soluble by substituting an alkali metal or alkaline earth metal sulfate or carboxylate salt onto the phthalocyanine structure have been found to be effective catalysts for the oxidation of aromatic compounds having benzylic carbon atoms to form the corresponding hydroperoxides.

5 Claims, No Drawings

USE OF WATER SOLUBLE METALLO PHTHALOCYANINES AS OXIDATION CATALYSTS

This invention relates to water soluble metallo phthalocyanine catalysts and to a process for the oxidation of aromatic compounds containing benzylic carbon atoms. More particularly this invention relates to the use of water soluble metallo phthalocyanine catalysts to improve the oxidation rate of aromatic compounds containing benzylic carbon atoms to form oxidation products such as hydroperoxides.

Aromatic compounds containing benzylic carbon atoms have been oxidized to hydroperoxides by autooxidation simply by passing oxygen through a solution of the compound. The rate of such oxidations are increased when carried out in the presence of salts or oxides of heavy metals. The conversion rate is only about 3 percent per hour and the product is normally contaminated with decomposition by-products such as acetophenone.

Metallo phthalocyanine catalysts for the oxidation of alkyl aromatic compounds are known. Such catalysts are not soluble in aqueous or organic media to any great extent and thereby show limited activity when employed in oxidations because of the heterogeneous nature of the reaction.

Metallo phthalocyanine catalysts have heretofore been employed at levels of from 0.5 to 3 percent by weight based on the weight of the total reactants and thereby have been extremely expensive. Rendering these materials water soluble increases their activity considerably because of the increased availability of the catalyst to the reactants.

About a 10 percent aqueous phase containing a base such as sodium hydroxide in solution to act as a phenol and organic acid scavenger is normally used in the autooxidation of benzylic hydrocarbons. Such scavengers in themselves improve oxidation rates since phenols are strong inhibitors of oxidation reactions, while organic acids serve to lower the reaction mixture pH to a level where the rearrangement of hydroperoxide to phenolic compounds becomes significant. Hydroperoxides are useful as initiators in free radical polymerizations.

It is therefore an object of the present invention to provide an improved process for the oxidation of aromatic compounds containing benzylic carbon atoms. Other objects will become apparent to those skilled in this art as the description proceeds.

It has been found in accordance with the present invention that the rate of oxidation of benzylic carbon atoms to the corresponding hydroperoxides can be substantially improved when a metallo phthalocyanine containing carboxylic acid or sulfonic acid groups in the form of an alkali metal salt or an alkaline earth metal salt is used as a catalyst.

The catalysts employed in this process are formed by combining a metallo phthalocyanine with a sulfonating agent such as chlorosulfonic acid or sulfuric acid monohydrate in combination with fuming sulfuric acid. Variations of basic phthalocyanine compounds and methods of preparation can be found in "Phthalocyanine Compounds," Moser and Thomas, pp. 193–213 (1963).

Metallo phthalocyanines which are effective in the practice of the present invention are those having metals with variable oxidation states. Metals which are most effective are manganese, iron, cobalt, nickel, copper, zinc and lead.

Oxidations conducted with the metallo phthalocyanine catalysts normally have the catalyst added to the aqueous phase of the reactor charge. Generally the weight of the metal contained in the catalyst compared to the weight of the reactants will not be less than 0.1 part per million and not greater than 50 parts per million. The preferred range is from about 0.5 part per million to about 10 parts per million.

The oxidation reactions can be initiated by free radical initiators present in concentrations ranging from one weight percent to ninety weight percent based on the weight of the reactants.

Preferred free radical initiators are those selected from the group consisting of alkyl hydroperoxides having from 4 to 6 carbon atoms, cycloalkyl hydroperoxides having from 6 to 12 carbon atoms and aralkyl hydroperoxides having from 8 to 14 carbon atoms. Representative examples of free radical initiators useful in this invention are t-butyl hydroperoxide, 2-methyl-2-hydroperoxy pentane, cumene hydroperoxide, ethyl benzene hydroperoxide, p-diisopropyl benzene monohydroperoxide, m-diisopropyl benzene monohydroperoxide, p-diisobutyl hydroperoxide, methyl cyclopentene hydroperoxide, methyl cyclohexane, p-menthane hydroperoxide and 1-isopropyl-4-ethyl cyclohexane hydroperoxide.

The invention is more concretely described with reference to the examples below, in which all parts and percentages are by weight unless otherwise specified. Catalysts useful in the practice of the present invention can be prepared as shown in Examples 1 and 2, in which copper phthalocyanine sodium sulfonate and copper phthalocyanine sodium carboxylate, respectively, were prepared. These procedures are effective for the preparation of various metal phthalocyanines.

EXAMPLE 1

Copper phthalocyanine sodium sulfonate was prepared from five grams of copper phthalocyanine and 100 grams of dichlorobenzene. The compounds were placed into a 250 milliliter flask fitted with the reflux condenser and magnetic stirrer. The mixture was heated to 100° C. under a nitrogen atmosphere to exclude water. Five cubic centimeters of chlorosulfonic acid (Eastman Chemical Company practical grade) were added to the reaction mixture. The temperature of the mixture was raised to 190° C. and maintained for three hours. The reaction mixture was then cooled to 95° C. and two cubic centimeters of water were added slowly to hydrolyze any remaining chlorosulfonic acid. Toluene was added to the reaction mixture to dissolve the dichlorobenzene forming a solid-liquid two-phase solution. All components except the sulfonated phthalocyanine were in liquid phase. The sulfonated phthalocyanine was filtered from the liquid phase as a solid. The solid was then washed with additional toluene to remove any remaining dichlorobenzene. The solid was slurried with water and sufficient sodium hydroxide to convert the acid form of the sulfonate to its sodium sulfonate. The phthalocyanine sodium sulfonate prepared in this manner was found to be completely water soluble in the desired catalyst range.

EXAMPLE 2

Copper phthalocyanine sodium carboxylic was prepared from pyromellitic dianhydride by placing 10 grams of pyromellitic dianhydride, 4 grams of copper chloride, 54 grams of urea and 25 milligrams of ammonium molybdate catalyst in a mortar, placing the mortar in a closed cabinet and blending the compounds together while under a nitrogen stream.

After blending, the compounds were heated using an oil bath for two hours under a continuous nitrogen stream at a temperature of from 180° C. to 185° C. The mixture was then washed with 125 milliliters of water and filtered. The filter cake was dissolved in 50 milliliters of sulfuric acid and added to 400 milliliters of cracked ice and water. A solid precipitated from solution and was filtered and washed with 400 milliliters of water until the pH was neutral and filtered until dry, forming a filter cake. The dry filter cake was placed in 200 milliliters of water and shaken until most of the filter cake was in solution. The solids were allowed to settle, filtered and air dried.

The product was a phthalocyanine containing some free carboxyl groups and having slight water solubility. The solubility was sufficient to allow complete solution of the catalyst at the levels used.

The oxidation of the aromatic compound having benzylic carbon atoms can be carried out as described in Example 3.

Examples 3, 4 and 5 show auto-oxidations carried out using sulfonated copper phthalocyanine sodium sulfate, cobalt phthalocyanine sodium sulfonate, and manganese phthalocyanine sodium sulfonate prepared as described in Example 1.

EXAMPLE 3

Para-diisopropyl benzene was oxidized by the following reaction. One hundred twenty-five cubic centimeters of p-diisopropyl benzene, 15 cubic centimeters of 2 weight percent sodium hydroxide in water, 100 milligrams of sulfonated copper phthalocyanine and 5 cubic centimeters of 70 percent t-butyl hydroperoxide in water were charged into a 300 cubic centimeter autoclave. The autoclave was closed and pressurized to 150 pounds per square inch gauge oxygen pressure and heated to 90° C. Samples were taken at 15 minute intervals. For each sample an iodometric titration was made. The iodine number measured dihydroperoxide equivalence which were reported in percent dihydroperoxide. The data from these samplings are presented in Table I.

Table I

| Reaction Time (minutes) | $I_2$ Number (% dihydroperoxide) |
|---|---|
| 0 | 4.84 |
| 15 | 15.2 |
| 30 | 22.3 |
| 45 | 32.5 |
| 60 | 36.8 |
| 75 | 40.8 |
| 90 | 43.7 |

The two percent sodium hydroxide serves to remove any phenols or carboxylic acids from the reaction system. Because of the presence of base, the acid catalyzed rearrangement of the hydroperoxide is minimized. Phenol (auto-oxidation inhibitors) are also formed as a result of the rearrangement. Any phenols formed are converted to their more readily oxidized sodium salt form. The t.butyl hydroperoxide acts as a free radical initiator. Small amounts of the hydroperoxide corresponding to the desired product can also be introduced into the reaction medium to act as a reaction initiator.

EXAMPLE 4

Manganese (II) phthalocyanine sodium sulfonate prepared as described in Example 1 was used as an oxidation catalyst for p-diisopropyl benzene in the same manner as described in Example 3. The results are shown in Table II.

Table II

| Reaction Time (minutes) | $I_2$ Number (% dihydroperoxide) |
|---|---|
| 0 | 10.5 |
| 15 | 17.4 |
| 30 | 22.6 |
| 45 | 26.9 |
| 60 | 31.4 |

EXAMPLE 5

Cobalt (II) phthalocyanine sodium sulfonate prepared as described in Example 1 was used as a catalyst in an oxidation of p-diisopropyl benzene in the same manner as described in Example 3. The results are shown in Table III.

Table III

| Reaction Time (minutes) | $I_2$ Number (% dihydroperoxide) |
|---|---|
| 0 | 9.7 |
| 15 | 18.7 |
| 30 | 24.8 |
| 45 | 28.3 |
| 60 | 31.4 |

Solubilizing metallo phthalocyanine catalyst in water systems increases the rate of the oxidation reaction as illustrated in Examples 6 and 7 below.

EXAMPLE 6

Example 6 was carried out under an oxygen pressure of 175 pounds per square inch gauge at 90° C. using 80 milligrams of copper phthalocyanine, 15 cubic centimeters of 2 weight percent sodium hydroxide and 135 cubic centimeters of a 5 weight percent solution of p-diisopropylbenzene monohydroperoxide. Samples were taken and tested as described in Example 3. The results are shown in Table IV.

Table IV

| Reaction Time (minutes) | $I_2$ Number (% dihydroperoxide) |
|---|---|
| 0 | 4.02 |
| 15 | 5.10 |
| 30 | 6.50 |
| 45 | 7.95 |
| 60 | 9.85 |
| 75 | 11.45 |
| 90 | 13.10 |
| 105 | 15.25 |

EXAMPLE 7

Example 7 was carried out in the same manner as described in Example 6 except that 137 milligrams of copper phthalocyanine sodium tetrasulfonate was used in place of the unsubstituted catalyst. Catalyst levels are calculated based on the weight of metal in the catalyst. The sodium tetrasulfonate increases the weight of catalyst necessary to have equal metal levels. Example 7 is thus a direct comparison to the results of Example 6. The results are shown in Table V.

Table V

| Reaction Time (minutes) | I₂ Number (% dihydroperoxide) |
|---|---|
| 0 | 4.50 |
| 15 | 5.60 |
| 30 | 8.50 |
| 45 | 12.70 |
| 60 | 19.10 |
| 75 | 24.50 |
| 90 | 29.00 |
| 105 | 34.00 |

Aromatic compounds having benzylic carbon atoms useful in the practice of the present invention have the general formula (I)

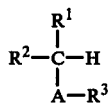

wherein $R^1$ and $R^2$ are the same or different radicals selected from the group consisting of hydrogen and alkyl radicals containing from 1 to 6 carbon atoms, or $R^1$ and $R^2$ can be taken together to form a cycloalkyl ring having from 4 to 7 carbon atoms, A is an aromatic neucleus and $R^3$ is selected from the group consisting of hydrogen, alkyl radicals having from 1 to 6 carbon atoms, halo radicals, acetyl radical, methoxy radical, organic acid esters and inorganic phosphates.

Representative examples of alkyl radicals in the above structural formula are methyl, ethyl, propyl and hexyl; of cycloalkyl radicals are cyclopentyl, cyclohexyl and cycloheptyl; of halo radicals are bromo, fluror, chloro and iodo; of organic esters are acetate, propionate and butyrate; and of compounds containing inorganic phosphates is p-isopropyl phenyl phosphate.

Representative examples of aromatic compounds containing benzylic carbon atoms useful in the present invention are ethyl benzene, cumene, sec-hexyl benzene, phenyl cyclohexane, phenyl cyclopentane, phenyl cycloheptane, p-disecbutyl benzene, m-disecbutyl benzene, p-t-butyl cumene, p-t-hexyl cumene, p-chloro cumene, p-bromo cumene, p-isopropyl acetophenone, p-methoxy cumene, p-isopropyl phenylacetate, p-sec-butyl phenyl acetate, p-isopropyl phenyl phosphate, sec-butyl benzene, m-diethyl benzene, p-diethyl benzene, o-cymene, m-cymene, p-diisopropyl benzene, m-diisopropyl benzene, α-isopropyl napthalene, β-isopropyl napthalene, p-t-butyl ethyl benzene, m-t-butyl ethyl benzene, p-phenyl cumene, m-phenyl cumene, chlorophenyl cumene, 1,1-diphenyl ethane, 1,1-ditolyl ethane, p-chloroethyl benzene and p-bromoethyl benzene.

Representative examples of the hydroperoxides that may be obtained using the process of the present invention are cumene hydroperoxide, cymene hydroperoxide, p-diisopropylbenzene monohydroperoxide, p-diisopropyl benzene dihydroperoxide, m-diisopropylbenzene dihydroperoxide, α-isopropylnapthylene hydroperoxide, β-isopropylnapthylene hydroperoxide and isobutylhydroperoxide.

Representative examples of catalysts useful in the practice of the present invention are water soluble metallo phthalocyanine catalysts such as copper phthalocyanine, manganese phthalocyanine, cobalt phthalocyanine, zinc phthalocyanine, nickel phthalocyanine and lead phthalocyanine. These catalysts are carboxylated or sulfonated, then further reacted to form the alkali or alkaline earth metal salt rendering the metallo phthalocyanine water soluble in the catalyst range desired. The sulfonates and carboxylates alone do not render the catalysts sufficiently water soluble to be effective.

Normally the phthalocyanine catalysts will have from one to five substitutions but from two to four are preferred. Although up to sixteen substitutions are possible, and the greater the substitution the greater the solubility, the low catalyst levels effective in this invention require only a low level of sulfonate or carboxylate alkali or alkaline earth metal salt substitution.

The process is normally carried out at a temperature of from 50° C. to 150° C. but the preferred temperature is from 80° C. to 140° C. and the most preferred temperature is from 90° C. to 120° C.

Normally a pressure of from 2 to 400 pounds per square inch gauge of oxygen is used but a pressure of from 50 to 200 pounds per square inch gauge is preferred. Higher pressures can be used, but the reaction benefits decrease and the reaction becomes less sensitive to pressure changes as the pressure is increased. No benefit is obtained above an oxygen partial pressure of about seven atmospheres.

During the course of the reaction sufficient aqueous caustic is used to maintain the pH of the reaction mixture between about 12 and about 6.5 to inhibit side reactions such as phenol and organic acid formations.

High levels of metallo phthalocyanine catalyst increase the rate of the oxidation reaction. The efficiency of the reaction, that is, the proportion of total reactant converted to the desired product, decreases as the level of catalyst is increased. Tables VI and VII compare the results of oxidizing p-diisopropyl benzene at 90° C. using 25 milligrams and 10 milligrams of copper phthalocyanine sodium tetrasulfonate respectively. In both Tables VI and VII, contractions of the following chemical names are used to indicate by-products, reactants and products.

DIPB: p-diisopropyl benzene
PAC: p-isopropyl acetophenone
MOX: 2-(4-isopropylphenyl)-2-hydroperoxy propane
MONOL: 2-(4-isopropylphenyl)-2-propanol
DAB: 1,4-diacetyl benzene
MOXA: 4-(α-methyl-α-hydroperoxyethyl)acetophenone
PAIPOL: 4-(α-methyl-α-hydroxyethyl)acetophenone
DIX: 1,4-bis(1-methyl-1-hydroperoxyethyl) benzene
MOXOL: 1-(α-methyl-α-hydroperoxyethyl)-4-(α-methyl-α-hydroxyethyl) benzene
DIOL: 1,4-bis(1-methyl-1-hydroxyethyl) benzene Samples of the reaction were taken at 15 minute intervals and analyzed using liquid elution chromatography.

Table VI

| | 25 Milligrams Catalyst | | | | | | | | | |
|---|---|---|---|---|---|---|---|---|---|---|
| Minutes | % DIPB | % PAC | % MOX | % MONOL | % DAB | % MOXA | % PAIPOL | % DIX | % MOXOL | % DIOL |
| 15 | 72.8 | 0.02 | — | — | — | 0.01 | 0.02 | 2.71 | 1.4 | 1.9 |
| 30 | 66.9 | 0.03 | 7.5 | — | 0.03 | 0.07 | — | — | 1.3 | 2.9 |

Table VI-continued

| | 25 Milligrams Catalyst | | | | | | | | | |
|---|---|---|---|---|---|---|---|---|---|---|
| Minutes | % DIPB | % PAC | % MOX | % MONOL | % DAB | % MOXA | % PAIPOL | % DIX | % MOXOL | % DIOL |
| 45 | 65.4 | 0.03 | 17.9 | — | 0.01 | 0.04 | 0.02 | 6.4 | 0.7 | 3.2 |
| 60 | 53.9 | 0.12 | 24.1 | — | 0.01 | 0.03 | 0.15 | — | 2.6 | 6.4 |
| 75 | 46.7 | 0.19 | 31.9 | — | — | 0.05 | 0.03 | 3.0 | 1.6 | 0.4 |
| 90 | 40.8 | 0.27 | 35.7 | 1.2 | — | 0.12 | 0.04 | 5.4 | 0.9 | — |
| 105 | 40.7 | 0.39 | 47.7 | 5.4 | 0.01 | 0.14 | 0.02 | 4.4 | 1.1 | 1.4 |
| 120 | 32.7 | 0.43 | 43.6 | 3.7 | — | 0.18 | 0.02 | 7.5 | 3.4 | 0.8 |

Table VII

| | 10 Milligrams Catalyst | | | | | | | | | |
|---|---|---|---|---|---|---|---|---|---|---|
| Minutes | % DIPB | % PAC | % MOX | % MONOL | % DAB | % MOXA | % PAIPOL | % DIX | % MOXOL | % DIOL |
| 15 | 75.9 | 0.02 | 9.5 | — | 0.06 | 0.03 | 0.05 | 5.4 | 4.6 | — |
| 30 | 82.1 | 0.02 | 7.0 | — | 0.03 | 0.02 | 0.02 | 0.7 | 2.4 | 2.5 |
| 45 | 67.5 | 0.06 | 16.5 | — | — | 0.05 | 0.04 | 1.1 | — | 0.8 |
| 60 | 52.8 | 0.07 | 21.0 | — | — | — | — | 6.1 | — | — |
| 75 | 55.1 | 0.10 | 29.0 | — | 0.03 | 0.02 | 0.01 | 11.7 | — | — |
| 90 | 48.3 | 0.11 | 37.5 | 4.9 | 0.01 | 0.02 | — | 3.2 | — | 4.7 |
| 105 | 47.0 | 0.15 | 34.5 | — | 0.01 | 0.04 | 2.1 | 0.6 | 2.8 | — |
| 120 | 44.1 | 0.19 | 37.6 | — | 0.01 | 0.05 | 0.02 | 3.0 | 2.0 | — |

While certain representative embodiments and details have been shown for the purpose of illustrating the invention, it will be apparent to those skilled in this art that various changes and modifications may be made therein without departing from the spirit or scope of the invention.

I claim:

1. In the hydroperoxide oxidation of an aromatic compound having the general structural formula (I)

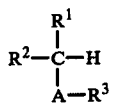

wherein $R^1$ and $R^2$ are the same or different radicals selected from the group consisting of hydrogen, alkyl radicals containing from 1 to 6 carbon atoms, or $R^1$ and $R^2$ can be taken together to form a cycloalkyl ring having from 4 to 7 carbon atoms, A is an aromatic nucleus and $R^3$ is selected from the group consisting of hydrogen, alkyl radicals having from 1 to 6 carbon atoms, halo radicals, acetyl radicals and methoxy radicals in the presence of a metallo phthalocyanine catalyst at a temperature of from 50° C. to 150° C. at a pressure of from atmospheric pressure to 500 pounds per square inch gauge oxygen partial pressure, the improvement comprising first rendering the metallo phthalocyanine catalyst water soluble by sulfonation using a combination of a material selected from the group consisting of (A) chlorosulfuric acid or (B) sulfuric acid monohydrate combined with fuming sulfuric acid.

2. A method as described in claim 1 wherein the water soluble metallo phthalocyanine catalyst is selected from the group consisting of alkali or alkaline earth metal sulfonates of copper phthalocyanine, manganese phthalocyanine, cobalt phthalocyanine, iron phthalocyanine and zinc phthalocyanine.

3. A method as described in claim 1 wherein (I) is selected from the group consisting of sec.butyl benzene, ethyl benzene, cumene, o-cymene, p-cymene, m-cymene, isopropylnaphthalene, p-diisopropyl benzene, m-diisopropyl benzene and phenyl cyclohexane.

4. A method as described in claim 1 wherein the catalysts are employed at a concentration of from .1 part per million to about 50 parts per million based on the weight of the reactants and the weight of metal contained in the catalyst.

5. A method as described in claim 4 wherein the oxidation reaction is initiated by a free radical initiator selected from the group consisting of alkyl hydroperoxides having from 4 to 6 carbon atoms and aralkyl hydroperoxides having from 8 to 14 carbon atoms in a concentration of from one weight percent to ninety weight percent and in the presence of sufficient sodium hydroxide to maintain the pH of the reaction mixture between about 12 and about 6.5.

* * * * *